(12) United States Patent
Diehl et al.

(10) Patent No.: US 9,366,602 B2
(45) Date of Patent: Jun. 14, 2016

(54) PARTICULATE MATERIAL SAMPLE DIVIDER

(71) Applicants: Jason K. Diehl, Winnipeg (CA); Dimo Karamichalis, Winnipeg (CA)

(72) Inventors: Jason K. Diehl, Winnipeg (CA); Dimo Karamichalis, Winnipeg (CA)

( * ) Notice: Subject to any disclaimer, the term of this patent is extended or adjusted under 35 U.S.C. 154(b) by 414 days.

(21) Appl. No.: 13/920,522

(22) Filed: Jun. 18, 2013

(65) Prior Publication Data

US 2014/0366652 A1 Dec. 18, 2014

(51) Int. Cl.
*G01N 1/18* (2006.01)
*G01N 1/20* (2006.01)

(52) U.S. Cl.
CPC .. *G01N 1/18* (2013.01); *G01N 1/20* (2013.01); *G01N 2001/2021* (2013.01)

(58) Field of Classification Search
CPC .............................. G01N 1/20; G01N 1/2035
USPC ....................................................... 73/863.52
See application file for complete search history.

(56) References Cited

U.S. PATENT DOCUMENTS

| 4,672,856 | A | * | 6/1987 | Marrs | G01N 1/20 73/863.52 |
| 2004/0221557 | A1 | * | 11/2004 | Dunning | A01G 1/125 56/1 |
| 2006/0277714 | A1 | * | 12/2006 | Dunning | A01G 1/125 15/405 |

* cited by examiner

*Primary Examiner* — Hezron E Williams
*Assistant Examiner* — Rodney T Frank
(74) *Attorney, Agent, or Firm* — Ryan W. Dupuis; Kyle R. Satterthwaite; Ade & Company, Inc.

(57) ABSTRACT

A particulate material sample divider includes a separation cone extending downwardly and radially outwardly from a central apex to an annular bottom edge with separator baffles supported on an outer surface of the separation cone at circumferentially spaced apart positions so as to define alternate first and second channels extends downwardly and radially outwardly between respective adjacent pairs of the baffles. A hopper supported above the separation cone discharges the sample over the cone for separation into the first and second channels. Each second channel only communicates with a second collection area to an outer side of a divider wall between the bottom edge of the cone. Each first channel includes an aperture in the separation cone such that each first channel only communicates through the aperture to a first collection area at an inner side of the divider wall.

10 Claims, 4 Drawing Sheets

PRIOR ART

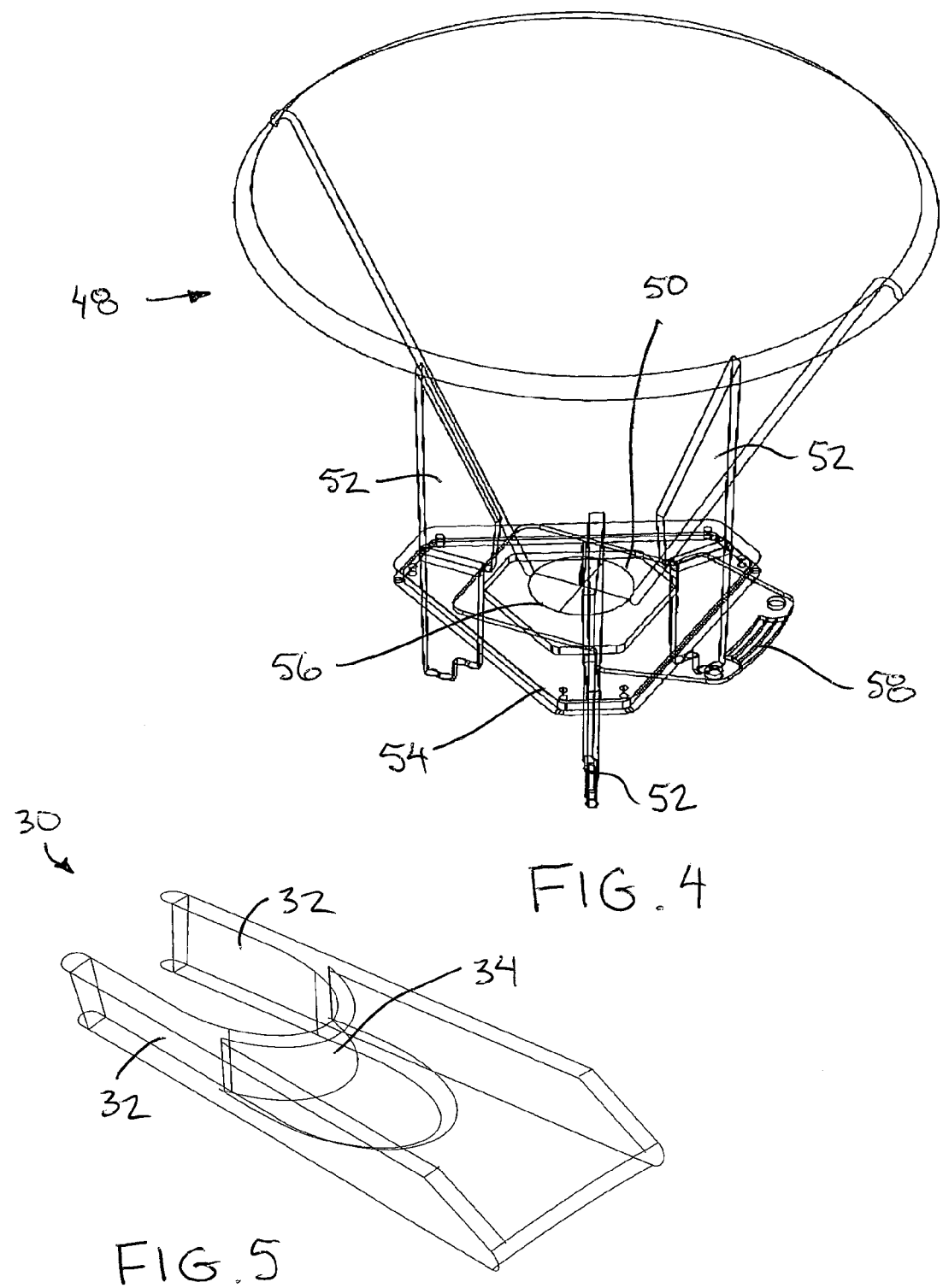

PARTICULATE MATERIAL SAMPLE DIVIDER

FIELD OF THE INVENTION

The present invention relates to a divider for dividing a sample of particulate material into two substantially identical portions.

BACKGROUND

In the field of agriculture, it is common to take samples of various grains to measure various conditions indicative of the quality of the grain. To perform different tests, it is often desirable to separate a given sample of grain into two equal parts with an even distribution of grain among each of the two parts. A known device for separating a sample into two equal parts is a Boerner-type divider. The divider is gravity operated so that a sample placed in an upper hopper is released by a valve to be evenly disbursed over a cone with evenly spaced separations. A complex manifold structure redirects the separated streams of grain into an inner funnel and an outer funnel respectively which empty into two separate collecting pans which at the bottom. While very effective, the configuration of the Boerner-type divider involves a very complex arrangement of parts to form the manifold structure which is accordingly very costly to manufacture.

SUMMARY OF THE INVENTION

According to one aspect of the invention there is provided a sample divider for dividing particulate material into two portions, the divider comprising:

a separation cone extending downwardly and radially outwardly from a central apex to an annular bottom edge;

a hopper supported above the separation cone so as to taper downwardly and inwardly towards a discharge opening at a bottom end of the hopper which is centrally located above the central apex of the separation cone;

a gate member supported at the bottom end of the hopper so as to be operable relative to the discharge opening between an open position and a closed position;

a plurality of separator baffles supported on an outer surface of the separation cone at circumferentially spaced apart positions so as to define a plurality of first channels and a plurality of second channels in which each of the first and second channels extends downwardly and radially outwardly between an adjacent pair of the separator baffles;

an annular divider wall extending downwardly from the bottom edge of the separation cone so as to define a first collection area adjacent an inner side of the divider wall and a second collection area adjacent an outer side of the divider wall;

each second channel extending to the bottom edge of the separation cone such that each second channel only communicates with the second collection area; and an aperture in the separation cone in alignment with each first channel such that each first channel is in communication only with the first collection area through the respective aperture in the separation cone.

By providing a cone with separator baffles which further comprises apertures aligned with only the first channels, a very simple structure permits re-directing material to interior and exterior sides of the separating cone, while maintaining all of the effectiveness of prior art devices. The simplified structure is thus easier to manufacture and is considerably less costly for the user.

Preferably an end wall spans generally circumferentially between the adjacent pair of separator baffles of each first channel adjacent to the respective aperture in the separation cone. Each end wall may be integral with the respective adjacent pair of separator baffles as a seamless, unitary body.

Preferably a cover cone is mounted above the separator cone to extend downwardly and radially outwardly from a central top opening aligned with the central apex of the separator cone. In this instance the separator baffles fully span a gap between the outer surface of the separator cone and a corresponding inner surface of the cover cone.

Preferably a bottom wall spans a bottom end of the annular divider wall to enclose a bottom end of the first collection area. When an outer wall is provided which is annular about the divider wall to define the second collection area in the annular space therebetween, preferably a bottom wall also spans a bottom end of the annular space to enclose a bottom end of the second collection area.

Preferably at least one of the separator baffles which is between one of the first channels and one of the second channels is adjustable at a top end in the circumferential direction so as to be arranged vary a ratio of particularly material diverted to the first and second collection areas respectively. Preferably a threaded member is in threaded connected between said at least one of the separator baffles and an adjacent baffle so as to be arranged to vary the spacing between said at least one of the separator baffles and the adjacent baffle as the threaded member is rotated.

One embodiment of the invention will now be described in conjunction with the accompanying drawings in which:

BRIEF DESCRIPTION OF THE DRAWINGS

FIG. 4 is a perspective view of the hopper assembly;

FIG. 5 is a perspective view of one of the baffle modules.

In the drawings like characters of reference indicate corresponding parts in the different figures.

DETAILED DESCRIPTION

Figure 1:
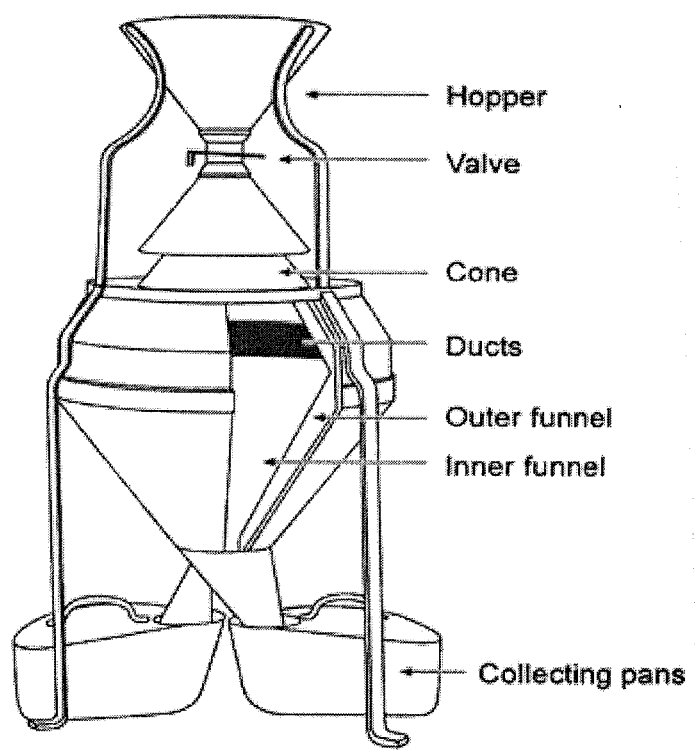
FIG. 1 is a perspective view of a Boerner-type divider.
Figure 2:
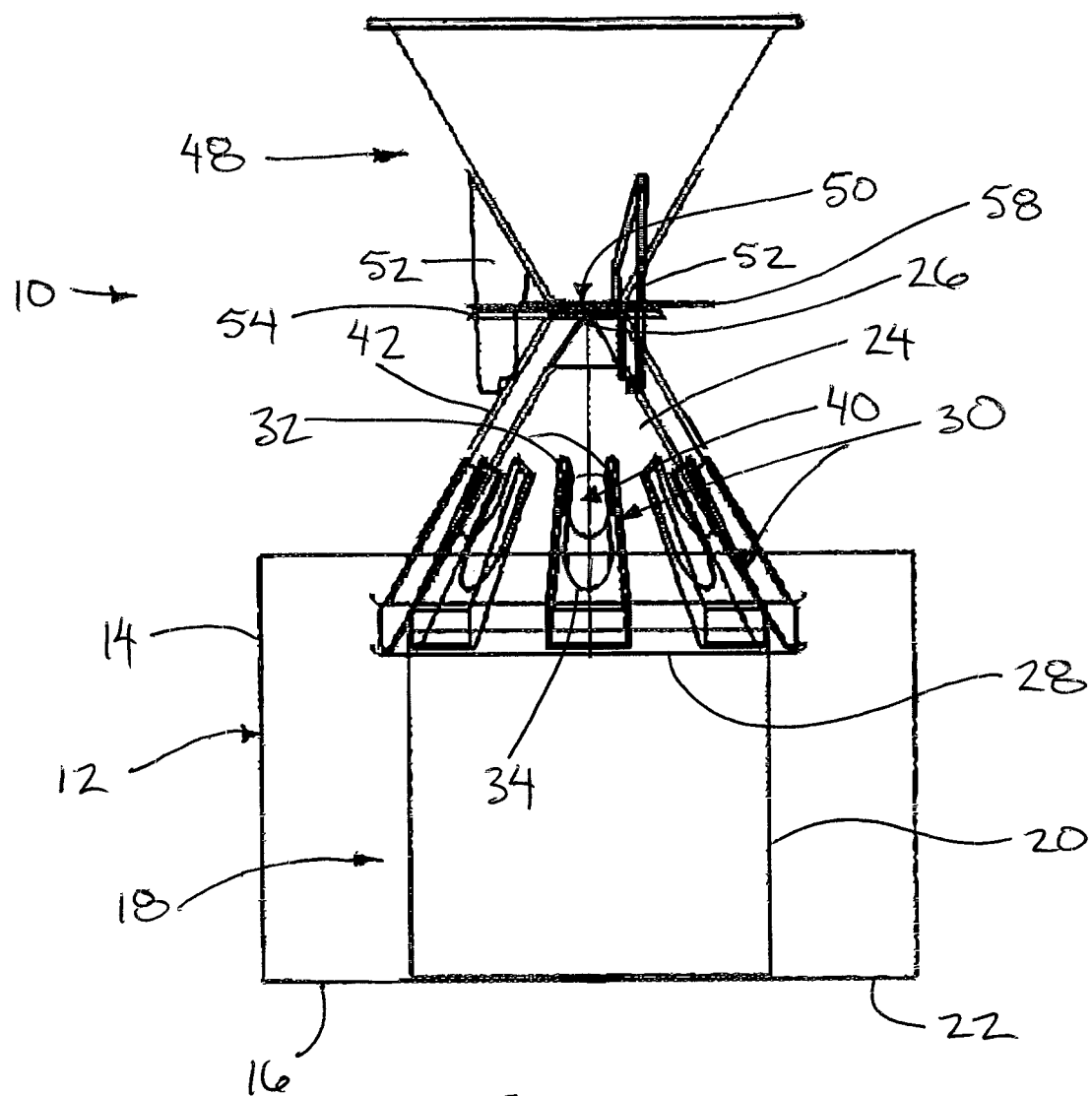
FIG. 2 is a partly sectional elevational view of the sample divider according to the present invention.
Figure 3:
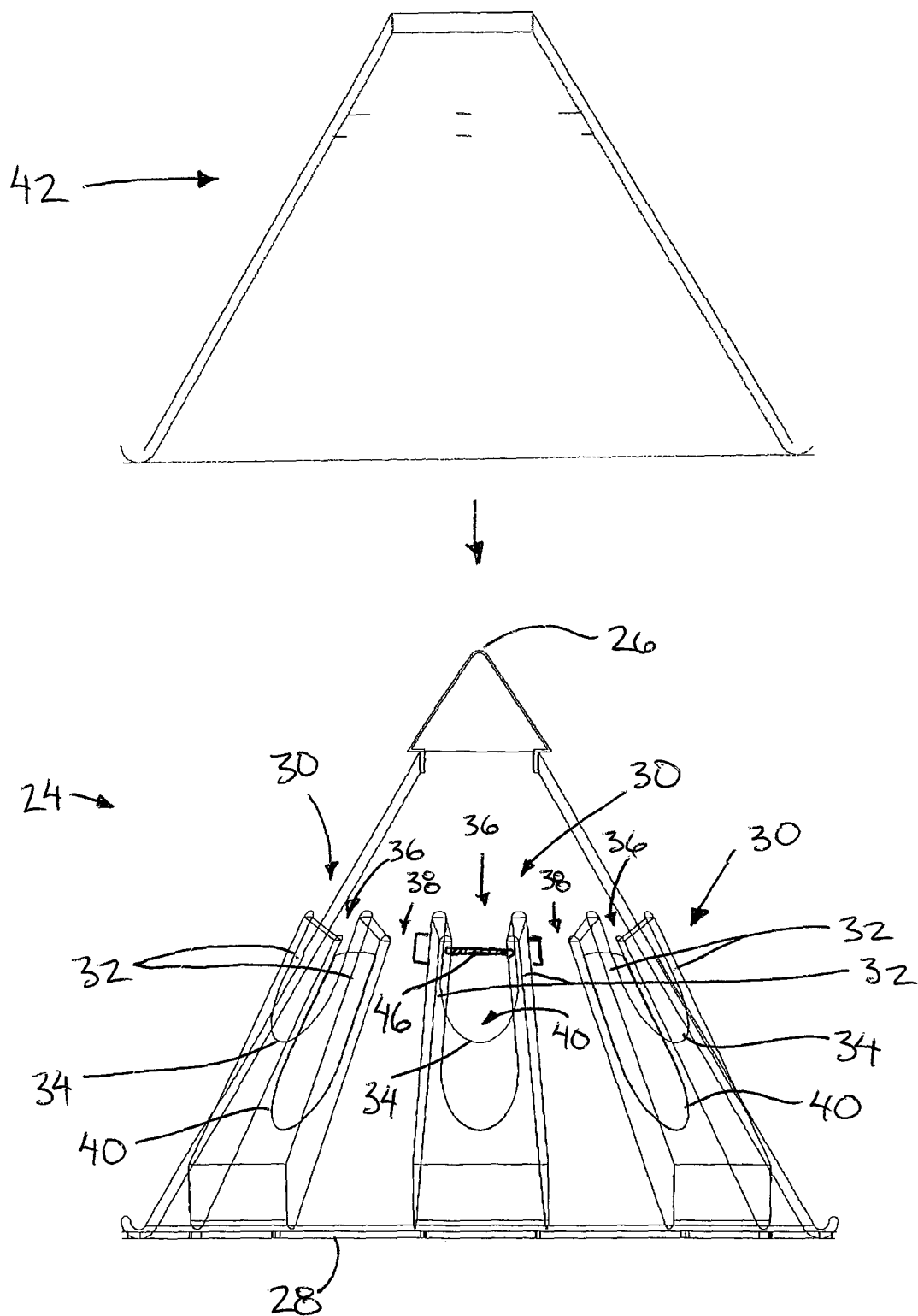
FIG. 3 is a side elevational view of the separation cone with the cover cone shown thereabove in a disassembled configuration.

Referring to the accompanying FIGS. 2 through 5 there is illustrated a sample divider generally indicated by reference numeral 10. The divider 10 is suited for use in dividing a grain sample into two equal samples with a substantially uniform distribution of grain in each sample.

The divider 10 includes an outer pail 12 comprising an upright cylindrical wall 14 enclosed at a bottom end by a bottom wall 16 to receive one of the separated samples therein. An inner pail 18 is nested within the outer pail and similarly includes a cylindrical wall 20 enclosed at the bottom end by a bottom wall 22. The inner pail is smaller in diameter than the outer pail such that the wall of the inner pail defines an annular divider wall which provides separation between a first collection area within the interior of the inner pail 18 and a second collection area defined as the annular space between the cylindrical walls of the inner and outer pails such that the second collection area extends circumferentially about the first collection area.

A separator cone 24 is mounted on the top edge of the cylindrical wall of the inner pail. The cone 24 has a generally inverted conical shape so as to taper downwardly and radially outwardly from a central apex 26 at the top end to a circular bottom edge lying in a horizontal plane at the bottom end 28. The bottom edge is similar in diameter as the annular divider wall so as to be supported thereon in use. An upper portion of the cone 24 which tapers to a central point at the apex is supported on the remaining lower portion so as to evenly distribute grain discharged thereon about the full circumference of the cone. The remainder of the cone below the upper portion forming the apex is moulded of plastic material. The upper portion 24 may be formed of a different material or include a coating of a different material thereon to improve the wear characteristics. In the preferred embodiment, the upper portion 24 is molded of plastic and coating with chrome for example.

A plurality of divider modules 30 are mounted on the outer surface of the lower portion of the separator cone to separate the grain sample into the first and second portions respectively. Each module 30 comprises two separator baffles 32 which are integrally joined together at their bottom ends by an end wall 34 such that the divider module is generally U-shaped and is moulded as a seamless, unitary one-piece moulded article. The divider modules are mounted at circumferentially spaced positions relative to one another such that all of the separator baffles 32 are generally evenly spaced apart in the circumferential direction to extend generally radially downwardly and outwardly towards the bottom edge at respective positions about the circumference. Furthermore, each baffle projects generally perpendicularly outward from the corresponding portion of the conical outer surface of the separator cone at the respective mounting location thereof.

The separator baffles 32 are arranged such that each adjacent pair of the baffles about the full circumference defines a respective channel therebetween which extends generally downwardly and radially outwardly. The channels include first channels 36 and second channels 38 which alternate with one another in the circumferential direction. Each first channel is defined between the adjacent pair of separator baffles 32 of a common divider module 30 such that the first channels are located at circumferentially spaced apart locations about the separation cone relative to one another and the second channels are similarly located at circumferentially spaced apart locations about the separation cone relative to one another. Alternatively, each second channel 38 is defined between two adjacent separator baffles 32 which are part of two adjacent but separate ones of the divider modules 30. The second channels remain uninterrupted from the top end to the bottom edge of the separator cone 24 so as to communicate only with the second collection area at the outer side of the annular divider wall 20.

Each first channel is associated with a respective aperture 40 formed in the wall of the separator cone to communicate from the outer surface to the inner surface thereof. Each aperture 40 is aligned with the respective first channel to span the full width thereof in the circumferential direction as well as to span substantially a full length of the channel between the top end of the respective separator baffles 32 and the end wall 34 located at the bottom edge of the aperture 40. The end wall is oriented to be sloped downwardly and inwardly towards the aperture such that no shelf-like surface is defined in the first channel by the respective divider module 30. Accordingly, each first channel only communicates with the first collection area through the respective aperture in the cone.

The divider further comprises a cover cone 42 in an inverted cone shape which has the same slope as the separator cone so as to mount over top of the separator cone, but at a location spaced thereabove so as to define a gap between the outer surface of the separator cone and the inner surface of the cover cone. The separator baffles 32 and the end walls of the modules are all arranged to span the full dimension of the gap extending perpendicularly outward from the outer surface of the separator cone towards the inner surface of the cover cone.

The cover cone includes a central opening 44 at the apex of the cover cone so as to be aligned with the apex of the separator cone. The top ends of the baffles are spaced downwardly and radially outward in relation to the top edge of the cover cone defining the perimeter of the central opening 44. Accordingly material discharged overtop of the apex of the separator cone is directed initially into an upper portion of the gap between the cover cone and the separator cone prior to reaching the baffles which subsequently evenly separates the material into the first collection area and second collection area respectively.

The divider modules 30 are mounted such that the circumferential distance between the top ends of two baffles of a common divider module are substantially equal to the circumferential space between two baffles of two adjacent divider modules. The mouth of the first channels collectively is thus approximately equal to the mouth of the second channels collectively as measured in the circumferential direction.

To provide some calibration or adjustment to ensure that the material is evenly divided into the first and second collection areas, a calibration mechanism can be provided. In this instance, the two baffles 32 of one of the divider modules remain flexible so that they are movable at the top ends relative to the cover cone and separator cone in the circumferential direction. A screw 46 is threadably connected between the two adjacent baffles in such a manner that turning the screw in one direction urges the two baffles towards one another, while rotating the screw in the opposing direction flexes the two baffles away from one another. When the two baffles of a common divider module are flexed together, the cross-sectional area of the respective first channel is reduced and the corresponding adjacent second channels are increased in dimension. The reverse occurs as the two baffles are pulled apart. In this instance, the ratio of material directed to the first channels collectively and the second channels collectively can be adjusted to perform a one-time calibration of the device at the time of manufacturing to ensure equal separation of the sample into two equal portions in the first and second collection areas respectively.

A hopper assembly 48 is mounted above the separator cone in which the hopper comprises a funnel or cone-shaped surface extending downwardly and radially inwardly to a central discharge opening 50 at the bottom end thereof. Three legs 52 are provided at circumferentially spaced positions to span generally vertically between the hopper thereabove and the cover cone therebelow. The discharge opening is positioned to be in close proximity to the central opening at the top of the cover cone with a similar diameter thereto. The discharge opening of the hopper is also arranged to be substantially concentric or coaxial with the apex of the separator cone.

A support plate 54 spans horizontally between the legs at a location between the hopper thereabove and the cover cone therebelow in direct abutment with the top end of the cover cone. A central opening 56 in the support plate aligns with the central opening 44 of the cover cone therebelow and the discharge opening 50 of the hopper thereabove.

A gate member 58 is supported on the support plate in the form of a flat panel which is slidable across the upper surface of the support plate between an open position in which the discharge opening of the hopper is unobstructed by the gate panel and a closed position in which the gate panel fully spans across and encloses the hopper discharge opening. The gate member 58 fits snuggly between the support plate 54 and the discharge opening of the hopper thereabove such that the support plate is sufficient to hold the gate member in engagement with the perimeter of the hopper about the discharge opening so as to retain particulate material to be sampled in the hopper until desired to be released.

In use, a person initially places particulate material to be divided in the hopper with the gate member in the closed position. Quickly pulling the gate member open permits all of the material in the hopper to be evenly discharged over the apex of the separator cone therebelow whereby the material flowing down the outer surface of the separator cone is contained by the cover cone and is subsequently evenly split between first and second channels respectively. Material in the first channels falls through the apertures in the cone to be collected within the first collection area to the interior of the divider wall while material in the second channels is directed to the bottom of the separator cone where it is directed to the second collection area at the exterior of the divider wall.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A sample divider for dividing particulate material into two portions, the divider comprising:
    a separation cone having a conical outer surface extending downwardly and radially outwardly from a central apex to an annular bottom edge;
    a hopper supported above the separation cone so as to taper downwardly and inwardly towards a discharge opening at a bottom end of the hopper which is centrally located above the central apex of the separation cone;
    a gate member supported at the bottom end of the hopper so as to be operable relative to the discharge opening between an open position and a closed position;
    a plurality of separator baffles supported on the separation cone to protrude outwardly from the conical outer surface of the separation cone at circumferentially spaced apart positions so as to define a plurality of first channels at circumferentially spaced apart locations about the separation cone relative to one another and a plurality of second channels at circumferentially spaced apart locations about the separation cone relative to one another, in which each of the first and second channels extends downwardly and radially outwardly between a respective adjacent pair of the separator baffles;
    an annular divider wall extending downwardly from the separation cone in proximity to the annular bottom edge of the separation cone so as to define a first collection area adjacent an inner side of the divider wall and a second collection area adjacent an outer side of the divider wall which is generally annular in shape about the first collection area;
    each second channel extending to the bottom edge of the separation cone such that each second channel only communicates with the second collection area; and
    an aperture in the separation cone in alignment with each first channel such that each first channel is in communication only with the first collection area through the respective aperture in the separation cone.

2. The divider according to claim 1 wherein there is provided an end wall spanning generally circumferentially between the adjacent pair of separator baffles of each first channel adjacent to the respective aperture in the separation cone.

3. The divider according to claim 2 wherein each end wall is integral with the respective adjacent pair of separator baffles as a seamless, unitary body.

4. The divider according to claim 1 further comprising a cover cone mounted above the separator cone to extend downwardly and radially outwardly from a central top opening aligned with the central apex of the separator cone, the separator baffles fully spanning a gap between the outer surface of the separator cone and a corresponding inner surface of the cover cone.

5. The divider according to claim 1 further comprising a bottom wall spanning a bottom end of the annular divider wall to enclose a bottom end of the first collection area.

6. The divider according to claim 1 further comprising an outer wall which is annular about the divider wall to define the second collection area in an annular space between the annular divider wall and the outer wall and a bottom wall spanning a bottom end of the annular space to enclose a bottom end of the second collection area.

7. The divider according to claim 1 wherein at least one of the separator baffles which is between one of the first channels and one of the second channels is adjustable at a top end in the circumferential direction so as to be arranged vary a ratio of particulate material diverted to the first and second collection areas respectively.

8. The divider according to claim 7 further comprises a threaded member in threaded connected between said at least one of the separator baffles and an adjacent baffle so as to be arranged to vary a spacing between said at least one of the separator baffles and the adjacent baffle as the threaded member is rotated.

9. A sample divider for dividing particulate material into two portions, the divider comprising:
    a separation cone extending downwardly and radially outwardly from a central apex to an annular bottom edge;
    a hopper supported above the separation cone so as to taper downwardly and inwardly towards a discharge opening at a bottom end of the hopper which is centrally located above the central apex of the separation cone;
    a gate member supported at the bottom end of the hopper so as to be operable relative to the discharge opening between an open position and a closed position;
    a plurality of separator baffles supported on an outer surface of the separation cone at circumferentially spaced apart positions so as to define a plurality of first channels and a plurality of second channels in which each of the first and second channels extends downwardly and radially outwardly between an adjacent pair of the separator baffles;
    an annular divider wall extending downwardly from the separation cone in proximity to the annular bottom edge of the separation cone so as to define a first collection area adjacent an inner side of the divider wall and a second collection area adjacent an outer side of the divider wall;
    each second channel extending to the bottom edge of the separation cone such that each second channel only communicates with the second collection area; and
    an aperture in the separation cone in alignment with each first channel such that each first channel is in communication only with the first collection area through the respective aperture in the separation cone;
    wherein at least one of the separator baffles which is between one of the first channels and one of the second channels is adjustable at a top end in the circumferential direction so as to be arranged vary a ratio of particulate material diverted to the first and second collection areas respectively.

10. The divider according to claim 9 further comprises a threaded member in threaded connected between said at least one of the separator baffles and an adjacent baffle so as to be arranged to vary a spacing between said at least one of the separator baffles and the adjacent baffle as the threaded member is rotated.

* * * * *